United States Patent [19]

Layton

[11] 4,217,911
[45] Aug. 19, 1980

[54] CYSTOMETRY SYSTEM

[75] Inventor: Terry N. Layton, Arlington Heights, Ill.

[73] Assignee: The Kendall Company, Boston, Mass.

[21] Appl. No.: 955,723

[22] Filed: Oct. 27, 1978

[51] Int. Cl.³ .............................................. A61B 10/00
[52] U.S. Cl. ................................... 128/748; 128/674; 128/214 E
[58] Field of Search ............... 128/650, 673, 674, 675, 128/748, 774, 778, 214 E

[56] References Cited

U.S. PATENT DOCUMENTS

| | | | |
|---|---|---|---|
| 1,666,332 | 4/1928 | Hirsch | 128/748 X |
| 2,558,190 | 6/1951 | Miller | 128/748 X |
| 3,828,781 | 8/1974 | Rothman | 128/304 X |
| 3,834,372 | 9/1974 | Turney | 128/748 |
| 3,934,576 | 1/1976 | Danielsson | 128/674 |
| 4,063,553 | 12/1977 | Karsh | 128/214 E X |
| 4,072,146 | 2/1978 | Howes | 128/674 |
| 4,077,405 | 3/1978 | Haerten et al. | 128/214 E X |

OTHER PUBLICATIONS

"Urogate" Cystometer Set, No. 4860, Publ. of Abbott Laboratories, Chicago, Ill.

Primary Examiner—Kyle L. Howell
Attorney, Agent, or Firm—Powell L. Sprunger

[57] ABSTRACT

A cystometry system to measure the pressure-volume relationship in the bladder of a patient from a source of fluid comprising, a catheter having an elongated shaft defining an infusion lumen communicating with an infusion opening adjacent a distal end of the shaft, and a pressure lumen communicating with a pressure opening adjacent the distal end of the shaft. The system has a device for supplying a selected volume of fluid from the source to the bladder through the infusion lumen of the catheter, and a device for measuring the bladder pressure through the catheter pressure lumen.

9 Claims, 5 Drawing Figures

CYSTOMETRY SYSTEM

BACKGROUND OF THE INVENTION

The present invention relates to medical measuring devices, and more particularly to cystometry systems.

Urologists commonly measure the static pressure-volume relationship in the bladder of patients, termed cystometrograms, in order to determine the capacitance of the bladder as a function of pressure and volume. During the procedure, the physician infuses a known volume of fluid, such as water or gas, into the bladder, and measures the resulting pressure in the bladder. The physician repeats this procedure a number of times while adding additional fluid volumes, and records the resulting pressure and volume data on a suitable graph. The physician may then use the pressure-volume curve to determine possible neurogenic and paralytic bladder dysfunctions.

SUMMARY OF THE INVENTION

A principal feature of the present invention is the provision of an improved cystometry system of simplified construction.

The cystometry system of the present invention comprises, a catheter having an elongated shaft defining an infusion lumen communicating with an infusion opening adjacent a distal end of the shaft, and a pressure lumen communicating with a pressure opening adjacent the distal end of the shaft. The device has a syringe, and a valve assembly which permits passage of fluid from the supply to the syringe and prevents passage of fluid from the syringe to the supply. The valve assembly permits passage of fluid under pressure from the syringe to the infusion lumen and prevents passage of fluid between the infusion lumen and the supply. The system has a manometer communicating with the catheter pressure lumen.

A feature of the present invention is that a selected volume of fluid may be aspirated from the supply through the valve assembly into the syringe.

Still another feature of the invention is that the selected volume of fluid may be pumped from the syringe through the valve assembly into the catheter infusion lumen and the patient's bladder.

Yet another feature of the invention is that the manometer may be utilized to directly determine the pressure in the bladder through the pressure lumen.

Thus, a feature of the invention is that selected volumes of fluid may be readily determined and pumped into the patient's bladder through use of the syringe.

Still another feature of the invention is that the bladder pressure may be determined by the manometer subsequent to each pumping step, such that the physician may readily ascertain the pressure relative to known variable amounts of fluid in the bladder for purposes of diagnosis.

Further features will become more fully apparent in the following description of the embodiments of this invention and from the appended claims.

DESCRIPTION OF THE PREFERRED EMBODIMENTS

Figure 1:
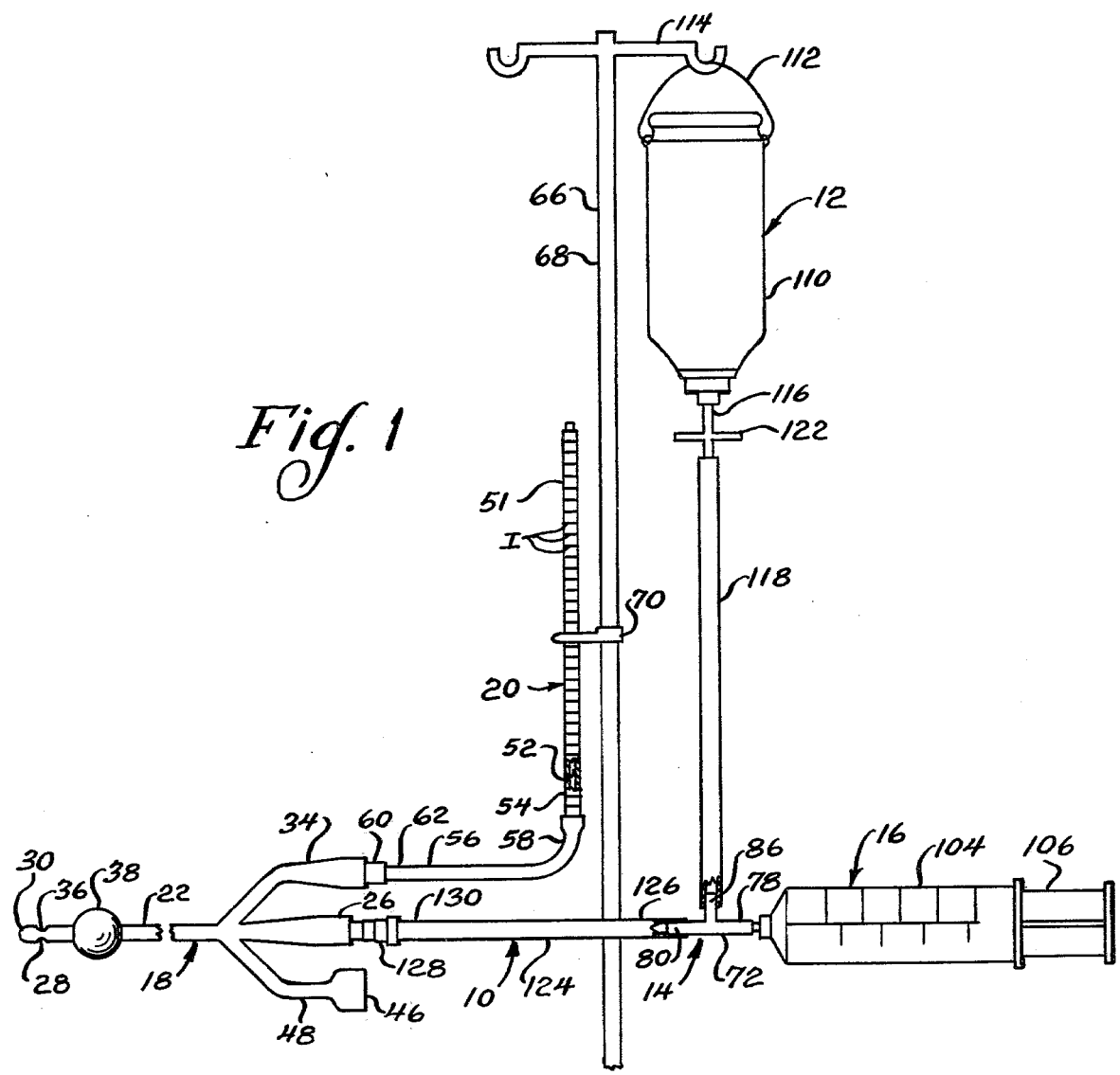
FIG. 1 is a fragmentary elevational view of a cystometry system of the present invention.
Figure 2:
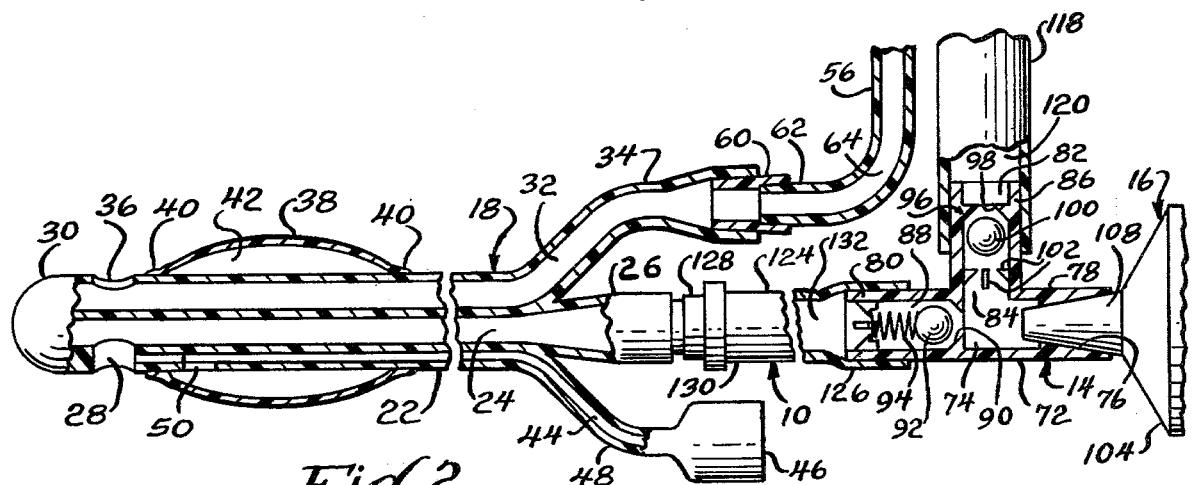
FIG. 2 is a fragmentary elevational view, taken partly in section, of the system of FIG. 1.

Referring now to FIGS. 1 and 2, there is shown a cystometry system generally designated 10 comprising a source of fluid 12, such as water, a valve assembly 14, a syringe 16, a catheter 18, and a manometer 20. The catheter 18 has an elongated shaft 22 defining an infusion lumen 24 extending from a proximal end 26 of the catheter 18 to an infusion opening 28 adjacent a distal end 30 of the catheter 18. The catheter shaft 22 also defines a pressure lumen 32 which extends through a first side arm 34 of the catheter adjacent the proximal end 26 of the catheter 18 to a pressure opening 36 adjacent the distal end 30 of the catheter 18. As shown, the catheter has an inflatable balloon 38 of elastic material having opposed ends 40 secured in circumferential zones to an outer surface of the catheter shaft 22, such that the balloon defines a cavity 42 intermediate the balloon 38 and the shaft 22. The catheter shaft 22 also defines an inflation lumen 44 extending from suitable valve means 46 at the proximal end of a second side arm 48 to an opening 50 communicating with the balloon cavity 42, such that the balloon 38 may be inflated through the valve means 46 and inflation lumen 44.

The manometer 20 may be of any suitable type, such as an elongated transparent tube 51 having a lumen 52 and pressure indicia I disposed longitudinally along the tube 51. As shown, the lower end 54 of the manometer 20 may be connected to the catheter pressure lumen 32 by a flexible conduit 56 having a proximal end 58 connected to the manometer lower end 54 and an adapter 60 at the distal end 62 of the conduit 56 received in the catheter side arm 34, such that a lumen 64 in the conduit 56 communicates between the manometer lumen 52 and the catheter infusion lamp 32. As shown, the manometer 20 may be supported on the upright post 66 of a suitable stand 68 through use of a clamp 70.

The valve assembly 14 has a housing 72 defining a first passageway 74 extending from a port 76 at the proximal end 78 of the housing 72 to a distal end 80 of the housing 72. The housing 72 also defines a second passageway 82 communicating with the first passageway 74 through an opening 84 intermediate the proximal and distal ends 78 and 80 of the housing 72, and extending to an outer end 86 of the housing 72. As shown, the valve assembly 14 has a first valve element 88 comprising a first valve seat 90 located distal the opening 84, a first valve member 92 comprising a ball, and a helical spring 94 supported in the first passageway 74 and biasing the valve member 92 in sealing engagement against the seat 90. Thus, the first valve element 88 is normally closed, and actuates above a predetermined pressure in the passageway 74 proximal the valve seat 90 for a purpose which will be described below. The valve assembly 14 also has a second valve element 96 comprising a second valve seat 98 in the second passageway 82, a second valve member 100 comprising a ball which may sealingly engage against the second seat 98, and a plurality of bosses 102 in the second passageway 82 which retain the valve member 100 intermediate the opening 84 and the second valve seat 98.

As shown, the syringe 16 has a barrel 104 and a plunger 106 slidably received in the barrel 104 to pump liquid into and out of the syringe. Also, the syringe has a tip 108 which is received in the port 76 at the proximal end 78 of the valve housing 72.

The source 12 may comprise a suitable hollow receptacle 110 for retaining the liquid. As shown, the receptacle 110 may have a suitable hanger 112 for supporting the receptacle 110 from a crossbar 114 of the stand 68. The lower end 116 of the receptacle 110 is connected to the outer end 86 of the valve housing 72 by a suitable flexible conduit 118 having a lumen 120 which communicates between the second passageway 82 of the valve assembly 14 and the receptacle 110. As shown, the system 10 may have an air filter 122 for venting the conduit lumen 120.

The system 10 may have a flexible conduit 124 having a proximal end 126 connected to the distal end 80 of the valve housing 72, and an adapter 128 at a distal end 130 of the conduit 124 received in the infusion lumen 24 at the proximal end 26 of the catheter 18. The conduit 124 has a lumen 132 which thus communicates between the first passageway 74 of the valve assembly 14 and the catheter infusion lumen 24.

In use, the distal end 30 of the catheter 18 is passed through the urethra of the patient until the openings 28 and 36 and balloon 38 are located in the patient's bladder, after which the balloon 38 is inflated through the valve means 46 and inflation lumen 44 in order to retain the catheter in place. Next, the clamp 122 may be released from the conduit 118 in order to permit passage of liquid from the receptacle 110 to the second passageway 82 of the valve housing 72, and through the open second valve element 96 to the first passageway 74. However, the spring 94 biases the first valve member 92 against the seat 90 with sufficient force to prevent opening of the first valve element 88 responsive solely to the pressure generated by the liquid passing from the container 110.

The physician may withdraw a selected volume of liquid into the syringe barrel 104 by manipulation of the plunger 106 while the second valve element 96 is in the open position. After the selected volume of liquid has been aspirated into the syringe 16, the physician pumps the syringe to eject the liquid from the syringe causing closure of the second valve element 96. Also, the pressure generated by the syringe causes the first valve element 88 to open, thus permitting passage of the pumped liquid through the first valve element 88, the conduit 124, and through the infusion lumen 24 and infusion opening 28 into the patient's bladder. After the selected volume of liquid has been pumped from the syringe into the patient's bladder, the biased first valve element 88 closes to prevent passage of liquid from the infusion lumen 24 past the first valve element 88. The liquid in the bladder then passes through the pressure opening 36 into the pressure lumen 32 and the manometer 20, such that the physician may readily ascertain the pressure in the bladder responsive to pumping the selected volume of liquid into the bladder. Thus, the physician may record both the selected volume of liquid and the resulting bladder pressure. The physician may repeat this procedure by pumping preselected volumes of liquid into the bladder a desired number of times, and recording the corresponding pressures generated in the bladder responsive to the separate pumping steps. The physician may record the pressure and volume data on a suitable chart after each pumping step has been completed for purposes of diagnosis.

Thus, in accordance with the present invention the cystometry system permits the physician to repetitively pump preselected volumes of liquid into the patient's bladder in a simplified and accurate manner. Further, the system permits the physician to readily ascertain the corresponding bladder pressures responsive to the pumping steps.

Figure 3:
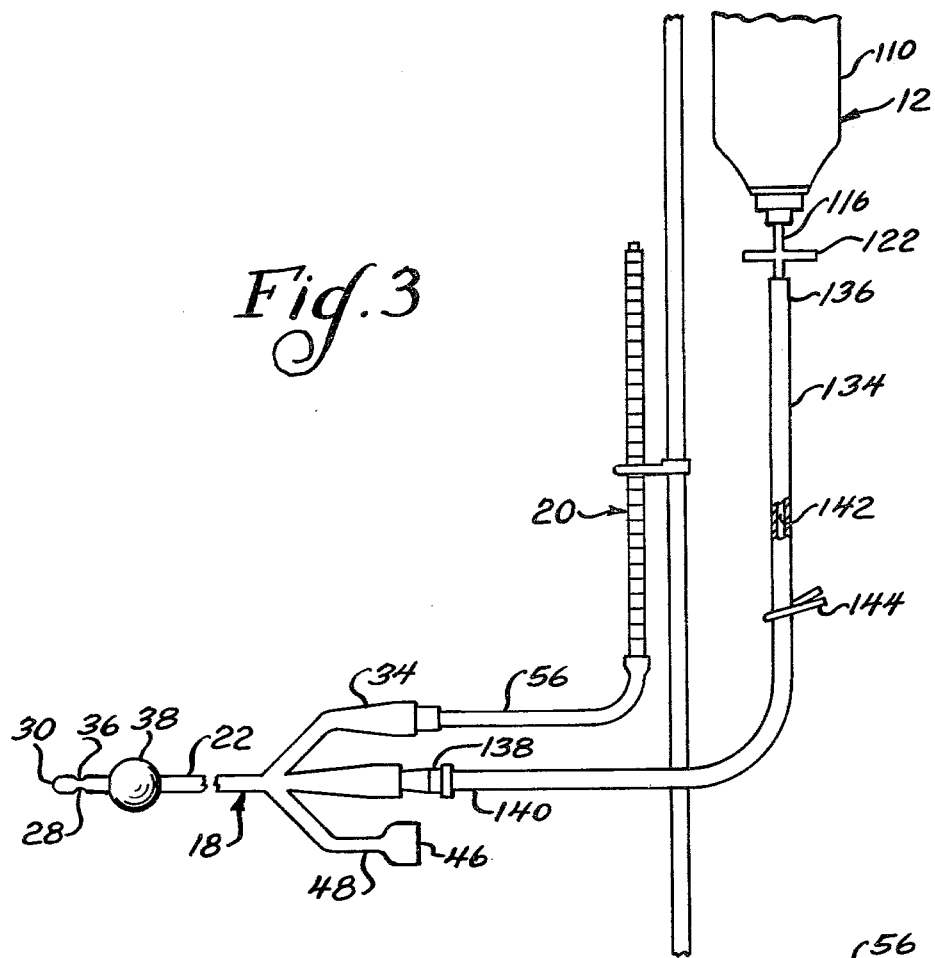
FIG. 3 is a fragmentary elevational view of another embodiment of a cystometry system of the present invention.

Another embodiment of the present invention is illustrated in FIG. 3, in which like reference numerals designate like parts. In this embodiment, the cystometry system 10 has a liquid source 12, a catheter 18, and a manometer 20 as previously described in connection with FIGS. 1 and 2. However, in this embodiment, the lower end 116 of the liquid receptacle 110 is connected directly to the infusion lumen at the proximal end 26 of the catheter 18 by a flexible conduit 134 having a proximal end 136 connected to the lower end 116 of the receptacle 110, and an adapter 138 at the distal end 140 of the conduit 134 received in the catheter infusion lumen, such that a lumen 142 in the conduit 134 communicates between the receptacle 110 and the catheter infusion lumen. The conduit 134 may also have a suitable clamp 144 to selectively open and close the conduit lumen 142. Thus, the clamp 144 may be opened to permit passage of a selected volume of liquid from the receptacle 110 through the conduit 134 and catheter infusion lumen into the patient's bladder, after which the clamp 144 is closed and the resulting pressure is determined by the manometer 20. The clamp 144 may be repetitively opened to permit passage of controlled amounts of liquid, and the resulting bladder pressures may be separately determined by the manometer 20 in order to obtain the pressure-volume data during the procedure.

Figure 4:
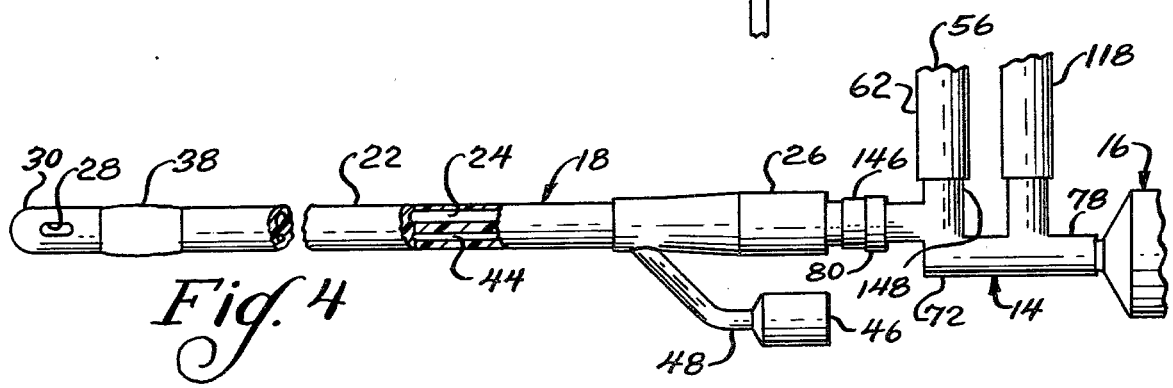
FIG. 4 is a fragmentary elevational view, taken partly in section, of another embodiment of a cystometry system of the present invention.
Figure 5:
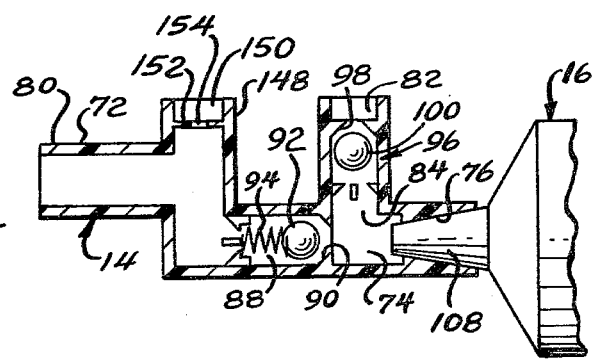
FIG. 5 is a sectional view of a valve assembly in the cystometry system of FIG. 4.

Another embodiment of the present invention is illustrated in FIGS. 4 and 5, in which like reference numerals designate like parts. In this embodiment, the catheter 18 has an infusion lumen 24 extending between the proximal end 26 of the catheter 18 and an infusion opening 28 adjacent the distal end 30 of the catheter shaft 22. Also, the catheter has an inflation lumen 44 communicating between an inflatable balloon 38 and valve means 46 on a side arm 48 of the catheter 18. However, in this embodiment, the catheter pressure lumen and corresponding pressure opening and side arm has been omitted.

The cystometry system 10 of FIGS. 4 and 5 also has a valve assembly 14 similar to that previously described in connection with FIGS. 1 and 2. Thus, the valve assembly 14 has a first passageway 74 which communicates from the port 76 through a first valve element 88 to an adapter 146 at the distal end 80 of the valve housing 72, with the adapter 146 being received in the infusion lumen 24 at the proximal end of the catheter 26 in order to establish communication between the first passageway 74 and the catheter infusion lumen 24. Of course, the first valve element 88 controls passage of fluid through the first passageway 74 in a manner as previously described in connection with FIGS. 1 and 2. The valve housing 72 of FIGS. 4 and 5 also has a second passageway 82 having a second valve element 96 similar to that previously described in connection with FIGS. 1 and 2. Also, the second passageway 82 communicates with the conduit 118 which extends from the liquid receptacle, as previously discussed in connection with FIGS. 1 and 2. Thus, the syringe 16 may be repetitively pumped to withdraw a selected volume of liquid from the supply, and eject the selected volume of liquid through the first valve element 88 and catheter infusion lumen into the patient's bladder, as previously discussed in connection with FIGS. 1 and 2.

However, in this embodiment, the valve housing 72 has an upwardly directed tubular section 148 defining a third passageway 150 communicating with the first passageway 74 distal the first valve element 88. Also, the tubular section 148 is connected to the distal end 62 of the conduit 56 extending from the lower end of the manometer, such that the conduit 56 establishes communication between the manometer and the third passageway 150 in the tubular section 148 of the valve housing 72. The tubular section 148 has an internal flange 152 defining a relatively small orifice 154 which limits passage of liquid through the third passageway 150 during pumping by the syringe 16. However, after the preselected volume of liquid has been pumped by the syringe through the first valve element 88 and the catheter into the patient's bladder, the liquid passes through the orifice 154 and through the conduit 56 to the manometer in order to determine the bladder pressure. Thus, in this embodiment, the manometer is connected through the valve assembly 14 to the infusion lumen of the catheter, rather than through a separate lumen of the catheter.

The foregoing detailed description is given for clearness of understanding only, and no unnecessary limitations should be understood therefrom, as modifications will be obvious to those skilled in the art.

I claim:

1. A system to measure the pressure-volume relationship in a body cavity of a patient, comprising:
    a source of fluid;
    a catheter having an elongated shaft defining an infusion lumen communicating with an infusion opening adjacent a distal end of the shaft, and a pressure lumen communicating with a pressure opening adjacent the distal end of the shaft;
    means for supplying a selected volume of fluid from the source to the cavity through the infusion lumen of the catheter comprising, pump means, and valve means communicating between said source, pump means, and infusion lumen, said valve means permitting passage of fluid from the supply to the pump means and preventing passage of fluid from the pump means to the supply, said valve means permitting passage of fluid under pressure from the pump means to the infusion lumen and preventing passage of fluid between the infusion lumen and the supply; and
    means for measuring the cavity pressure through the catheter pressure lumen.

2. The system of claim 1 wherein the pressure measuring means comprises a manometer communicating with the pressure lumen adjacent a proximal end of the pressure lumen.

3. The system of claim 1 wherein the catheter has an inflatable balloon adjacent the distal end of the shaft, and in which the shaft defines an inflation lumen communicating with the balloon.

4. The system of claim 1 including means for preventing passage of fluid from the supply to the infusion lumen below a predetermined pressure, and permitting passage of fluid above the predetermined pressure responsive to pressure generated by the pump means.

5. The system of claim 1 wherein the supplying means comprises a syringe, a valve assembly having a first passageway to receive a tip of the syringe adjacent a proximal end of the first passageway and communicating with the catheter infusion lumen through a distal end of the first passageway, and a second passageway communicating with the first passageway, said supplying means having a conduit communicating between an outer end of the second passageway and the supply, said valve assembly having a first valve element in the first passageway distal the second passageway, said first valve element being normally closed and opening responsive to pressure generated by the syringe to permit passage of fluid from the syringe to the catheter infusion lumen, and a second valve element in the second passageway permitting passage of fluid from the supply to the syringe and preventing passage of fluid from the syringe to the supply.

6. The system of claim 5 wherein the first valve element comprises a valve seat in the first passageway distal the second passageway, a valve member in the first passageway distal the seat, and means for biasing the valve member against the seat.

7. The system of claim 6 wherein the valve member comprises a ball, and in which the biasing means comprises a helical spring.

8. The system of claim 5 wherein the second valve element comprises a valve seat in the second passageway, and a valve member intermediate the seat and the first passageway.

9. The system of claim 8 wherein the valve member comprises a ball, and including means for retaining the ball in the proximity of the seat.

* * * * *